United States Patent
Armitstead

(10) Patent No.: US 8,985,106 B2
(45) Date of Patent: Mar. 24, 2015

(54) METHODS AND DEVICES FOR THE DETECTION OF HYPOPNOEA

(75) Inventor: Jeffrey Peter Armitstead, North Sydney (AU)

(73) Assignee: ResMed Limited (AU)

(*) Notice: Subject to any disclaimer, the term of this patent is extended or adjusted under 35 U.S.C. 154(b) by 1091 days.

(21) Appl. No.: 12/781,070

(22) Filed: May 17, 2010

(65) Prior Publication Data

US 2010/0307500 A1    Dec. 9, 2010

Related U.S. Application Data

(60) Provisional application No. 61/184,592, filed on Jun. 5, 2009.

(51) Int. Cl.
- *A61M 16/00* (2006.01)
- *A62B 7/00* (2006.01)
- *A61B 5/087* (2006.01)
- *A61B 5/00* (2006.01)

(52) U.S. Cl.
CPC ............... *A61M 16/00* (2013.01); *A61B 5/087* (2013.01); *A61B 5/4818* (2013.01); *A61M 16/0069* (2013.01); *A61M 2016/0039* (2013.01); *A61M 2205/505* (2013.01); *A61M 2230/205* (2013.01)
USPC .................................. 128/204.21; 128/204.23

(58) Field of Classification Search
USPC ........... 128/204.18, 204.21, 204.23; 600/529, 600/538
See application file for complete search history.

(56) References Cited

U.S. PATENT DOCUMENTS

| | | | |
|---|---|---|---|
| 5,295,490 A | 3/1994 | Dodakian | |
| 5,605,151 A | 2/1997 | Lynn | |
| 5,704,345 A * | 1/1998 | Berthon-Jones | 128/204.23 |

(Continued)

FOREIGN PATENT DOCUMENTS

| | | |
|---|---|---|
| CN | 101394884 A | 3/2009 |
| JP | 2007301372 A | 11/2007 |

(Continued)

OTHER PUBLICATIONS

Partial European Search Report, EP 10163967, dated Nov. 18, 2010.

(Continued)

*Primary Examiner* — Valerie L Skorupa
(74) *Attorney, Agent, or Firm* — Lerner, David, Littenberg, Krumholz & Mentlik, LLP

(57) ABSTRACT

Automated methods provide hypopnea detection for determining a hypopnea event and/or a severity of a hypopnea event. In some embodiments, a calculated short-term variance of a measured respiratory flow signal are compared to first and second proportions of a calculated long-term variance of the measured flow signal. A detection of the hypopnea may be indicated if the first measure falls below and does not exceed a range of the first and second proportions during a first time period. In some embodiments, a hypopnea severity measure is determined by automated measuring of an area bounded by first and second crossings of a short-term measure of ventilation and a proportion of a long-term measure. The detection methodologies may be implemented for data analysis by a specific purpose computer, a detection device that measures a respiratory airflow or a respiratory treatment apparatus that provides a respiratory treatment regime based on the detected hypopneas.

26 Claims, 7 Drawing Sheets

(56) References Cited

U.S. PATENT DOCUMENTS

| | | | |
|---|---|---|---|
| 5,797,852 A | | 8/1998 | Karakasoglu et al. |
| 5,961,447 A | | 10/1999 | Raviv et al. |
| 6,029,665 A | * | 2/2000 | Berthon-Jones ......... 128/204.23 |
| 6,138,675 A | * | 10/2000 | Berthon-Jones ......... 128/204.23 |
| 6,142,950 A | | 11/2000 | Allen et al. |
| 6,165,133 A | | 12/2000 | Rapoport et al. |
| 6,363,933 B1 | * | 4/2002 | Berthon-Jones ......... 128/204.23 |
| 6,367,474 B1 | * | 4/2002 | Berthon-Jones et al. 128/204.23 |
| 6,368,287 B1 | | 4/2002 | Hadas |
| 6,502,572 B1 | * | 1/2003 | Berthon-Jones et al. 128/204.23 |
| 7,118,536 B2 | | 10/2006 | Haberland et al. |
| 8,353,289 B2 | | 1/2013 | Farrugia et al. |
| 2003/0062044 A1 | * | 4/2003 | Berthon-Jones et al. 128/204.18 |
| 2004/0123866 A1 | * | 7/2004 | Berthon-Jones ......... 128/204.23 |
| 2005/0020932 A1 | | 1/2005 | Haberland et al. |
| 2005/0076910 A1 | * | 4/2005 | Berthon-Jones et al. 128/204.23 |
| 2006/0021618 A1 | * | 2/2006 | Berthon-Jones et al. 128/204.18 |
| 2006/0102179 A1 | * | 5/2006 | Rapoport et al. ........ 128/204.23 |
| 2008/0053440 A1 | * | 3/2008 | Farrugia ................... 128/204.23 |
| 2008/0163873 A1 | * | 7/2008 | Berthon-Jones ......... 128/204.23 |
| 2008/0294957 A1 | | 11/2008 | Tan et al. |
| 2009/0050155 A1 | * | 2/2009 | Alder et al. .............. 128/204.23 |

FOREIGN PATENT DOCUMENTS

| | | |
|---|---|---|
| WO | 2006047826 A1 | 5/2006 |
| WO | 2007101297 A1 | 9/2007 |
| WO | 2008/138040 A1 | 11/2008 |

OTHER PUBLICATIONS

U.S. Appl. No. 60/965,172, filed Aug. 17, 2007.

* cited by examiner

METHODS AND DEVICES FOR THE DETECTION OF HYPOPNOEA

CROSS REFERENCE TO RELATED APPLICATIONS

This application claims the benefit of the filing date of U.S. Provisional Patent Application No. 61/184,592 filed Jun. 5, 2009, the disclosure of which is hereby incorporated herein by reference.

FIELD OF THE TECHNOLOGY

The present technology relates to methods and apparatus for detection of hypopnea.

BACKGROUND OF THE TECHNOLOGY

Patients with OSA have recurrent apnoeas or hypopnoeas during sleep that are only terminated by the patient arousing. A hypopnea may be considered a partial reduction in breathing that lasts at least 10 seconds during sleep. The 1999 American Academy of Sleep Medicine (AASM) guidelines specify a hypopnea condition as a 10 second reduction in flow of 50% or more or a reduction of flow of less than 50% followed by an arousal or a desaturation of at least 3%. Subsequent AASM guidelines specify a 30% reduction in ventilation and a desaturation of at least 4% as a hypopnea condition. These recurrent events cause sleep fragmentation and stimulation of the sympathetic nervous system. This can have severe consequences for the patient including day-time sleepiness (with the attendant possibility of motor-vehicle accidents), poor mentation, memory problems, depression and hypertension. Patients with OSA are also likely to snore loudly, thus also disturbing their partner's sleep.

The best form of treatment for patients with OSA is constant positive airway pressure (CPAP) applied by a blower (compressor) via a connecting hose and mask. The positive pressure prevents collapse of the patient's airway during inspiration, thus preventing recurrent apnoeas or hypopnoeas and their sequelae. Such a respiratory treatment apparatus can function to supply the patient with a supply of clean breathable gas (usually air, with or without supplemental oxygen) at the therapeutic pressure or pressures, at appropriate times during the subject's breathing cycle.

Respiratory treatment apparatus typically include a flow generator, an air filter, a mask or cannula, an air delivery conduit connecting the flow generator to the mask, various sensors and a microprocessor-based controller. The flow generator may include a servo-controlled motor and an impeller. The flow generator may also include a valve capable of discharging air to atmosphere as a means for altering the pressure delivered to the patient as an alternative to motor speed control. The sensors measure, amongst other things, motor speed, gas volumetric flow rate and outlet pressure, such as with a pressure transducer, flow sensor or the like. The apparatus may optionally include a humidifier and/or heater elements in the path of the air delivery circuit. The controller may include data storage capacity with or without integrated data retrieval/transfer and display functions.

To treat hypopnea, automated apparatus have been implemented with algorithms to detect a hypopnea condition based on data from a flow sensor. Examples of conventional apnea/hypopnea detection devices are taught in U.S. Pat. No. 5,295,490 to Dodakian; U.S. Pat. No. 5,605,151 to Lynn; U.S. Pat. No. 5,797,852 to Karakasoglu et al.; U.S. Pat. No. 5,961,447 to Raviv et al.; U.S. Pat. No. 6,142,950 to Allen et al.; U.S. Pat. No. 6,165,133 to Rapoport et al.; U.S. Pat. No. 6,368,287 to Hadas; U.S. Pat. No. 7,118,536 to Haberland et al. For example, in one such device, a hypopnoea can be deemed detected if a 10 or 12 second root mean square (RMS) of a flow (in L/sec) signal drops below 1.2 times the long-term average minute ventilation (in L/sec) (e.g., low pass filtering the absolute value of a flow signal divided in half), which approximately corresponds to a reduction to 50% of the normal RMS ventilation. A 50% reduction of an RMS ventilation may also be detected by comparing a ten second variance of a flow signal calculated over a 10 second window with the product of $(0.5)^2$ and a sixty second variance of a flow signal calculated over a 60 second window. Such devices may also include a refractory period of time after detecting a hypopnea to prevent multiple scoring of a common hypopnea event. For example, the device may remain refractory for 15 seconds or until the RMS ventilation returns to at least three quarters of a long-term RMS ventilation for 15 contiguous seconds.

However, the question of the presence of a hypopnea condition itself is subject to interpretation. There is often considerable clinician variability in scoring the presence of a hypopnea. Thus, while automated apparatus may be implemented with various methods to detect the condition, differences in the implemented detection criteria can result in different hypopnea scoring for common breathing events.

It may be desirable to develop further methods for detecting hypopnea which may also be implemented in apparatus for detection and apparatus for treating upper respiratory conditions.

SUMMARY OF THE TECHNOLOGY

A first aspect of some embodiments of the present technology is to provide methods and devices for detecting a hypopnea and/or a severity of a hypopnea.

Another aspect of some embodiments of the technology is to detect hypopneas or hypopnea severity in an apparatus that measures a respiratory flow signal of a patient.

A still further aspect of the technology is to implement the detection of hypopnea or hypopnea severity in a respiratory treatment apparatus, such as a continuous positive airway pressure device, based on or as a function of the detected hypopneas or hypopnea severity.

Some embodiments of the present technology involve an apparatus or controller with a method for controlling a processor to detect a hypopnea from a measured flow of breathable gas. The method of the controller or processor may involve determining a first measure from a short-term variance of data based on a measured flow of breathable gas. It may further involve determining a second measure from a long-term variance of data based on a measured flow of breathable gas. The first measure may be compared with first and second proportions of the second measure. With the method, the apparatus or controller may indicate a detection of the hypopnea based on the comparing if the first measure falls below the first proportion and does not subsequently exceed a range of the first and second proportions during a first time period.

In some embodiments, the first proportion may be less than the second proportion and the method may also involve indicating a detection of a hypopnea if the first measure does not exceed the first proportion during the first time period. Moreover, the method may also involve indicating a detection of a hypopnea if the first measure exceeds the first proportion but does not exceed the second proportion during the first time period. In some embodiments, the comparing of the first measure and the first proportion represents a determination of whether an RMS value calculated from approximately ten to twenty seconds, but preferably twelve seconds, of respiratory flow data falls below a threshold of approximately fifty percent of an RMS value calculated from approximately fifty to seventy seconds, but preferably sixty seconds, of respiratory flow data and wherein the first period of time is approximately three to eight seconds, but preferably four seconds. Moreover, the comparing of the second measure and the second proportion may represent a determination of whether an RMS value calculated from approximately ten to fifteen seconds, but preferably twelve seconds, of respiratory flow data is below a threshold of approximately seventy five percent of an RMS value calculated from approximately fifty to seventy seconds, but preferably sixty seconds, of respiratory flow data.

Optionally, further detections of a hypopnea may be impeded until the first measure exceeds the second proportion during a second period of time. This impeding of a further detection may involve comparing of the first measure and the second proportion such that the comparing represents a determination of whether an RMS value calculated from approximately ten to fifteen seconds, but preferably twelve seconds, of respiratory flow data exceeds a threshold of approximately seventy five percent of an RMS value calculated from approximately fifty to seventy seconds, but preferably sixty seconds, of respiratory flow data and wherein the second period of time is approximately ten to twenty seconds but preferably fifteen, seconds. In some cases, the time from which the long term measure of ventilation is calculated may be at least approximately three to five times that of the time from which the short term measure is calculated.

Some embodiments of the present technology involve an apparatus or controller with a method for controlling a processor to detect a hypopnea from a measured flow of breathable gas. The method of the processor or controller may include determining a long-term measure of ventilation and a short-term measure of ventilation. The method of the processor or controller may further include determining a threshold as a proportion of the long-term measure of ventilation and measuring an area bounded by first and second crossings of the short-term measure of ventilation and the threshold. A hypopnea is then detected with the measured area. The measuring may involve integrating a difference between the threshold and the short-term measure of ventilation during a time period from when the short-term measure falls below the threshold to when the short-term measure exceeds the threshold. In some embodiments, the measuring comprises adding a plurality of sample differences during a time period from when the short-term measure falls below the threshold to when the short-term measure exceeds the threshold. Each sample difference may be a difference between a sample of the threshold and a sample of the short-term measure of ventilation.

Optionally, the method of the apparatus or controller may be configured to impede a further detection of a hypopnea during a refractory period initiated at the second crossing. Moreover, the method may include triggering the measuring of the area upon detecting the first crossing by comparing the short-term measure of ventilation and the threshold for inequality. Still further, the detecting of the hypopnea may be contingent upon a time from the first crossing to the second crossing exceeding about ten seconds. In some embodiments, the short-term measure of ventilation may be an output of low pass filtering half of an absolute value of a measure of flow of breathable gas with a first time constant. Similarly, the long-term measure of ventilation may be an output of low pass filtering half of an absolute value of a measure of flow of breathable gas with a second time constant larger than the first time constant. Optionally, the proportion may be set at approximately seventy percent. In some embodiments, the device or apparatus may indicate a severity of the hypopnea with the measure of area. Optionally, the device or apparatus may compare the measured area with a threshold chosen to be approximately indicative of a desaturation of blood oxygen of at least four percent.

Some embodiments of the present technology involve an apparatus or controller with a method for controlling a processor to detect a hypopnea from a measured flow of breathable gas that includes the controller or a processor determining a long-term measure of ventilation and a short-term measure of ventilation. A threshold is then determined as a proportion of the long-term measure of ventilation. The controller or processor then calculates an extent of a hypopnea as a function of the short-term measure of ventilation and the threshold. The apparatus then indicates a severity of the hypopnea with the measured extent, which may involve outputting a value of the measured extent. The calculated extent may be a calculated area bounded by first and second crossings of the short-term measure of ventilation and the threshold. The calculated area may then optionally be compared with a threshold chosen to be approximately indicative of a desaturation of blood oxygen of at least four percent.

In some embodiments, the method of the apparatus or controller may further detect a measure of flow limitation from a measured flow of breathable gas and wherein the indicating the detection of the hypopnea is further based on the measure of flow limitation being indicative of obstruction.

Still further embodiments of the technology may involve a methodology for controlling a processor to classify a hypopnea from a measured flow of breathable gas. The method of the processor may include detecting an hypopnea event from a measured flow of breathable gas. It may further include determining a measure indicative of obstruction in the measured flow coincident with the hypopnea event. The method may also include classifying the detected hypopnea event as obstructive or central based on the determining of the measure indicative of obstruction. In some such embodiments, the determining comprises detecting partial obstruction and the classifying comprises scoring an obstructive hypopnea event. In some such embodiments, the method may also involve detecting an absence of a breath and the classifying may involve scoring a central hypopnea event based on the absence of a breath. In an alternative embodiment, the method may also involve detecting an absence of a breath coincident with a detected hypopnea event and refraining from scoring the detected hypopnea event as either central hypopnea or obstructive hypopnea based on the absence of the breath. In such a case, the event may be considered to be an apnea.

In some embodiments, the technology may be implemented as a hypopnea detection apparatus. In such an apparatus, an included controller may have at least one processor to access data representing a measured flow of breathable gas. The controller may be configured to control a detection of an hypopnea event from the data representing the measured flow of breathable gas. It may also be configured to control a determination of a measure indicative of obstruction coincident with the hypopnea event in the data representing the measured flow. It may also be configured to control a classification of the detected hypopnea event as obstructive or central based on the determining of the measure indicative of obstruction. In some such embodiments, the classification detects partial obstruction and the classification comprises scoring an obstructive hypopnea event. In some such embodiments, the controller may be further configured to control a detection of an absence of a breath and the classification may involve scoring a central hypopnea event. In an alternative embodiment, the controller may determine an absence of a breath coincident with a detected hypopnea event and refrain from scoring the event as either central hypopnea or obstructive hypopnea based on the detected absence of the breath. In such a case, the event may be considered to be an apnea. Such an apparatus may also include a flow generator configured to produce a breathable gas for a patient at a pressure above atmospheric pressure and a flow sensor. The controller may then be configured to measure the flow of breathable gas with the flow sensor and to control the flow generator to produce the breathable gas according to a pressure therapy regime based on the detected hypopnea.

Additional features of the present respiratory technology will be apparent from a review of the following detailed discussion, drawings and claims.

BRIEF DESCRIPTION OF DRAWINGS

The present technology is illustrated by way of example, and not by way of limitation, in the figures of the accompanying drawings, in which like reference numerals refer to similar elements including.

DETAILED DESCRIPTION

Figure 1:
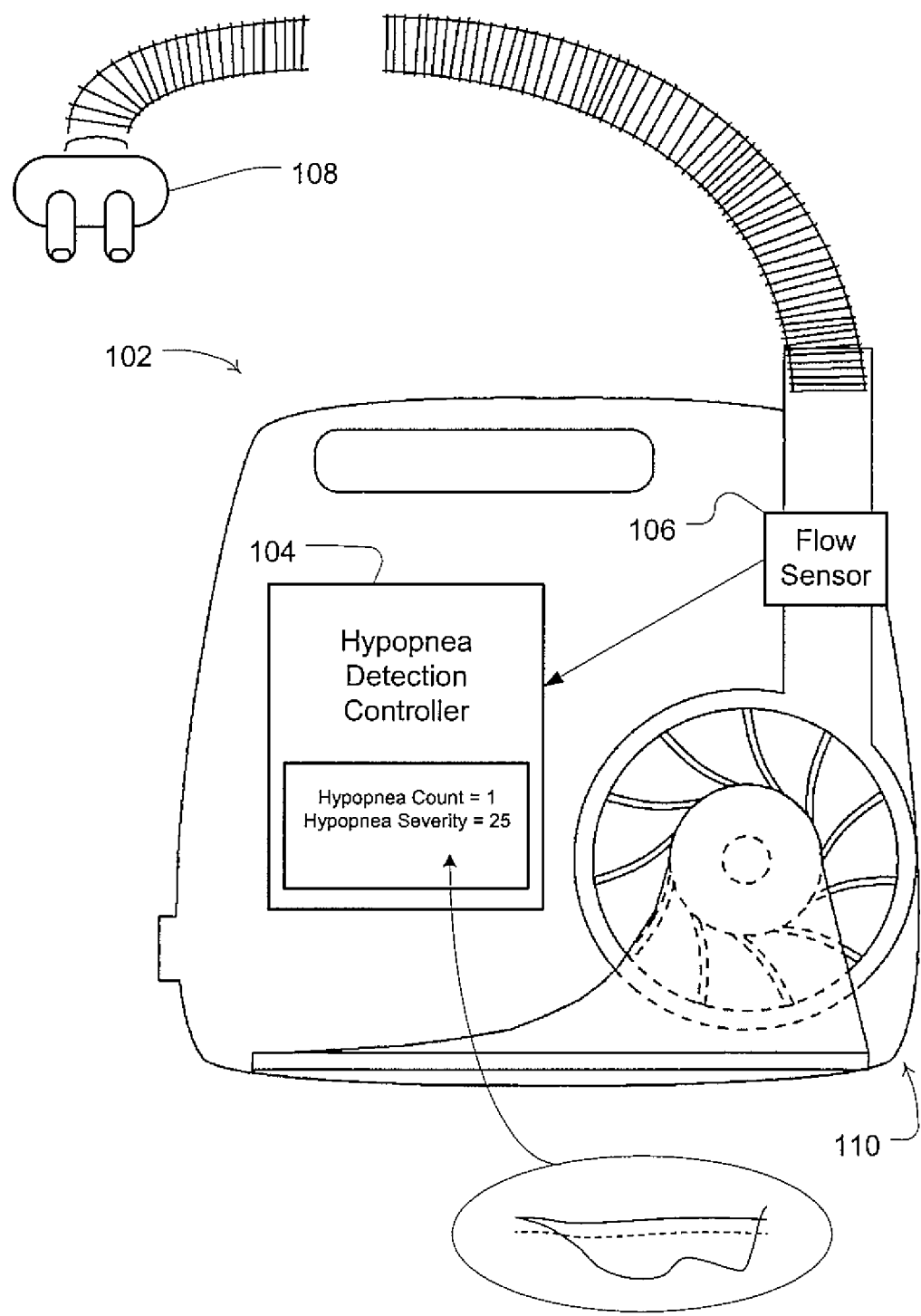
FIG. 1 shows an example hypopnea detection apparatus of the present technology with an optional flow sensor and flow generator.

As illustrated in FIG. 1, embodiments of the present technology may include a hypopnea detection device or apparatus having a controller 104 that may have one or more processors to implement particular hypopnea detection methodologies such as the algorithms described in more detail herein. Thus, the device or apparatus may include integrated chips, a memory and/or other control instruction, data or information storage medium. For example, programmed instructions encompassing such detection methodologies may be coded on integrated chips in the memory of the device or apparatus to form an application specific integrated chip (ASIC). Such instructions may also or alternatively be loaded as software or firmware using an appropriate data storage medium. With such a controller or processor, the device can be used for processing data from a flow signal. Thus, the processor may control the assessment of a hypopnea occurrence or severity as described in the embodiments discussed in more detail herein based on measured and recorded respiratory flow data from a prior sleep session. Alternatively, the detection may be performed during a sleep session contemporaneously with the measuring of a respiratory flow signal. Thus, in some embodiments, the device or apparatus itself may optionally be implemented with a flow sensor 106 for measuring a respiratory flow signal for use with the implemented methodologies. For example, flow to or through a nasal cannula 108 or mask may be measured using a pneumotachograph and differential pressure transducer or similar device such as one employing a bundle of tubes or ducts to derive a flow signal. Optionally, a flow signal may be inferred from other sensors, such as, a motor current sensor as described in PCT/AU2005/001688 filed on Nov. 2, 2005, and U.S. patent application Ser. No. 12/294,957, the National Stage thereof, the entire disclosures of which is incorporated herein by cross reference.

By way of further example, the hypopnea detection device may be implemented with a control methodology to respond to detected hypopnea as a respiratory treatment apparatus. For example, as illustrated in FIG. 1, detection device may be optionally implemented with a flow generator such as a servo controlled blower with suitable sensors for such control (e.g., a pressure sensor). A respiratory treatment or pressure therapy regime, such as a therapeutic pressure level associated with CPAP treatment, may be delivered by the controller of the device. Such therapeutic pressure levels may be automatically adjusted in response to the detection of hypopnea conditions as described herein. For example, pressure levels may be increased by a specified amount upon detection of a hypopnea. Optionally, it may be increased proportionally as a function of a detected hypopnea severity. For example, a hypopnea with a greater severity measure may yield a greater pressure adjustment then a hypopnea with a lesser severity measure. Other pressure adjustment schemes may also be implemented.

In some embodiments, the hypopnea detector may implement a detection of a hypopnea according to AASM guidelines. For example, the detector may be constructed to score a hypopnea event upon detection of a reduction in ventilation by about 30% or more for about 10 seconds or more coupled with the detection of a desaturation of blood oxygen by about 4% or more. In such an embodiment, the reduction in ventilation may, for example, be determined by a measure of ventilation such as a tidal volume or other such measure based on the measured respiratory flow signal. Optionally, the measure of ventilation may be derived by processing of determined breath peak inspiratory and/or breath peak expiratory flows. Similarly, the reduction of blood oxygen may be based on data from an oximetry signal from an optional oximetry sensor (not shown in FIG. 1). However, as discussed in more detail herein, other embodiments of the present technology may be implemented to emulate such an AASM guideline without analysis of oximetry data from an oximetry sensor.

(1) Example Detection Features

Figure 2:
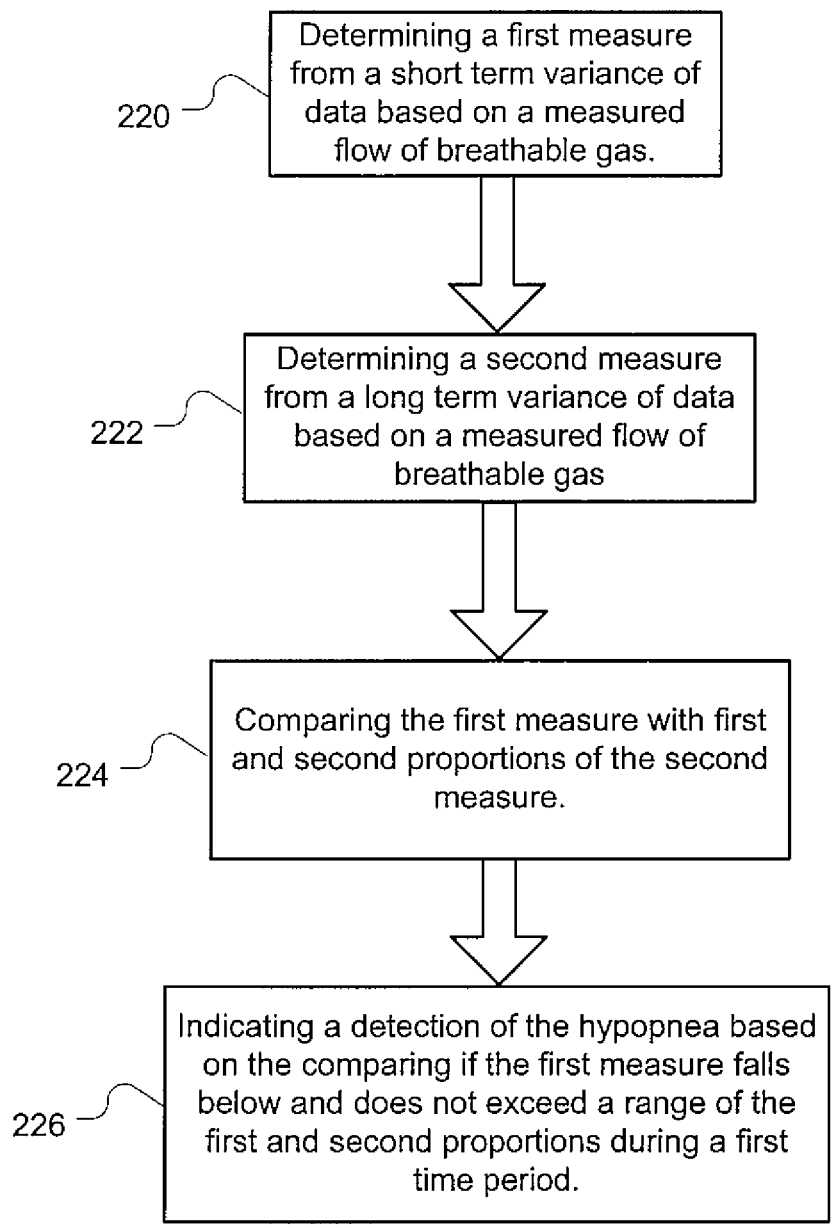
FIG. 2 is a flow diagram of an example embodiment of a method of controlling an apparatus to detect a hypopnea.

As illustrated in the flow chart of FIG. 2, in some embodiments of the present technology an automated detection of a hypopnea condition by a detection device may be based on the determination or calculation of a variance from data representing a measure of a flow of breathable gas or a respiratory flow signal. For example, at 220 a first measure from a short-term variance calculation may be determined. One such measure may be calculated by determining the mean of the squares minus the square of the mean of the samples from a respiratory flow signal from a flow sensor or recorded data based thereon. Other methods for calculating the variance may also be implemented. The short-term variance may be on the order of seconds, such as about ten to fifteen seconds, for example a 10 second variance utilizing about ten seconds of samples taken from the flow signal. Similarly, a long-term variance measure may be determined at 222. The long-term variance may be on the order of minutes such as approximately one minute or about fifty to seventy seconds, for example, 60 seconds utilizing about sixty seconds of samples taken from the flow signal. In some cases, the time from which the long term measure of ventilation is calculated may be at least approximately three to five times that of the time from which the short term measure is calculated. For example, is the long term measure of ventilation is chosen to be calculated from sixty seconds, the short term measure may be calculated as one fifth (e.g., 60/5) to give a time period of twelve seconds.

At 224, a measure of the short-term variance may be compared with first and second proportions of the long-term variance. For example, it may be desired to detect a hypopnea based on a decrease that does not exceed a certain range, for example, between of 45% and 70%. In such a case, the long-term variance may be multiplied by factors of $(0.45)^2$ and $(0.7)^2$. Optionally, these factors may be utilized without the squaring operations if they are multiplied by the square root of the long-term variance and the resulting proportions are compared with the square root of the short-term measure of variance. Such a comparison represents a determination of a reduction in airflow based on RMS ventilation. At 226, a hypopnea event may then be scored or indicated when the measure of the short-term variance falls below the first proportion but does not subsequently exceed a range of the first and the second proportions for a period of time. Such a system may permit more accurate automated detection or scoring of hypopnea, by permitting brief excursions of data of the respiratory flow signal above the first proportion but not the second while a time period of the fall in patient breathing is accumulated or timed.

Figure 3:
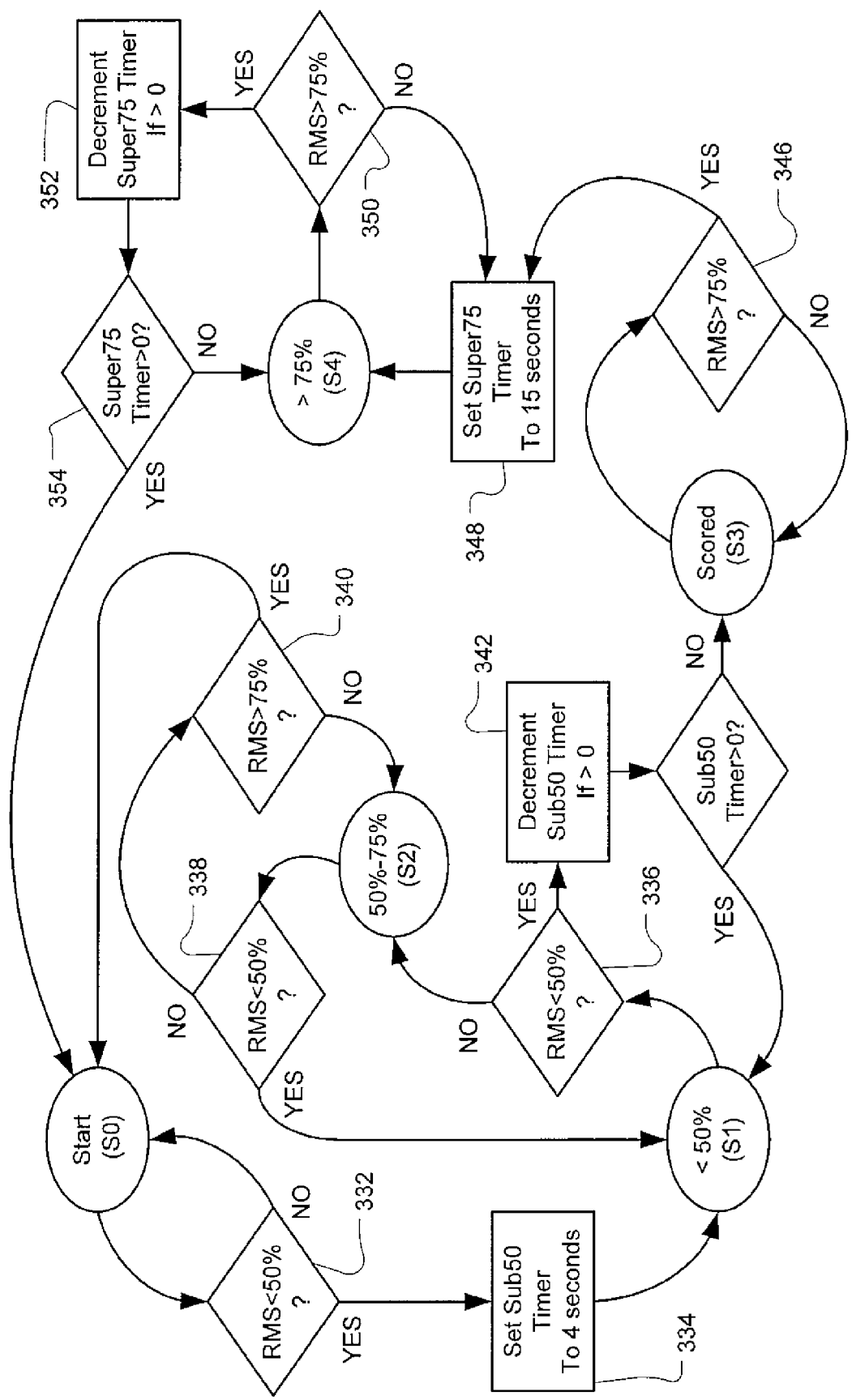
FIG. 3 is a state diagram of a further example apparatus that may implement a method of detecting a hypopnea.

A state diagram for implementing such an embodiment of the technology in a detector is illustrated in FIG. 3. The detector may be useful for a device that contemporaneously scores hypopnea during a sleep session with the detector while a patient is experiencing the event but it may also be implemented for post-session analysis. The behavior of the device begins at a start state S0. At 332, the device may determine whether the RMS ventilation falls below about a 50% threshold. For example, the device may compare a short-term variance of a respiratory flow signal determined over a 10 or 12 second data window (i.e., $V_{10}$ or $V_{12}$) with a proportion of a long-term variance determined over a sixty second data window (e.g., $(0.5)^2$ times $V_{60}$). If this threshold is met or breached, a timing period may be triggered or started at 334 and the device enters a sub-50 state (S1). For example, a count down timer (designated "Sub-50 Timer") may be set to a maximum period of about three to eight seconds, but preferably four seconds. Other values for this time setting may be pre-determined depending on the desired results of hypopnea evaluation criteria. If the threshold is not met at 332, the device returns to the start state (S0).

At 336, the device then determines whether the RMS ventilation remains below about 50%. Such a test may be comparable to the test implemented at 332. If not, then the device transitions to an excursion range state (S2). From this state, the device tests whether the RMS ventilation again falls below about 50% at 338. If it does, the device then returns to the sub-50 state (S1). If not, then the device tests whether the RMS ventilation exceeds about a 75% threshold at 340. For example, the device may compare the short-term variance of a respiratory flow signal determined over a 10 or 12 second data window (i.e., $V_{10}$ or $V_{12}$) with another proportion of the long-term variance determined over a sixty second data window (e.g., $(0.75)^2$ times $V_{60}$). If this threshold is met or breached, then the device may transition to the start state (S01) without scoring a hypopnea event. If at 340 the threshold is not met, then the device returns to the excursion range state (S2).

If at 336 the test determines that the RMS ventilation remains below about 50%, then the Sub-50 Timer is decremented or permitted to count down if it has not expired (e.g., if it greater than 0) at process block 342. Then, at 344, the Sub-50 Timer is checked for an expiration condition such that the timing period has expired or lapsed. If it has not expired the device remains in the sub-50 state (S1). If it has expired, the device scores a hypopnea upon entering the scored state (S3). Thus, detection device indicates a hypopnea condition based on the analysis of the sub-50 state (S1) and the excursion range state (S2).

Another feature of the device once having entered the scored state (S3) is the implementation of a refractory period to prevent multiple scoring of a common hypopnea event. Thus, at 346 the RMS ventilation is tested to see if it exceeds about a 75% threshold. The test is comparable to the comparison at 340. If at 346 it does not exceed the threshold, the device remains in the scored state (S3). If at 346 it does exceed the threshold, another timing period or a refractory timing period may be triggered or started at 348 and the device enters a super-75 state (S4). For example, a count down timer (designated "Super-75 Timer") may be set to a maximum period of about ten to twenty seconds, but preferably 15 seconds. Other values for this time setting may be pre-determined depending on the desired length of the refractory time to ensure that the scored hypopnea condition has ceased.

From the super-75 state (S4), the RMS ventilation is checked at 350 for confirmation that it remains above the threshold of about 75% like the comparison at 346. If it does, then at 352 the Super-75 Timer is decremented so it continues to run or count down. If at 354, the Super-75 Timer has expired or passed the desired time period, then the device returns to the start state (S0). If not, the device remains in the super-75 state (S4).

In sum, the detector determines whether the short-term ventilation measure falls below a 50% threshold and then stays there for about 4 seconds. The detector allows excursions above the 50% threshold but not a 75% threshold while the 4 second period is being accumulated. However, if the 75% threshold is exceeded before the accumulation period is over then the detector will reset to start without a hypopnoea indication. Once the accumulation is complete, a hypopnoea is indicated. The detector then requires the short-term threshold measure to exceed a 75% threshold for a refractory period such as 15 contiguous seconds before the detector becomes non-refractory. As implemented, the detector will not score short hypopnoeas and will tend to allow messy periods of depressed flow to be scored as one hypopnoea rather than two or more.

In some embodiments, entering the stored state (S3) or otherwise indicating or scoring a hypopnea may be further conditioned on a detection of flow limitation, an obstructive apnea and/or central apnea, which may be detected by a common processor as the hypopnea detection processor or a different processor in electronic communication with the hypopnea detection processor. For example, the device may be configured to also detect an obstructive apnea, partial obstruction and/or central apnea by any of the methods described in U.S. Pat. Nos. 6,138,675 and 6,029,665, the entire disclosures of which are incorporated herein by cross reference, which a different processor or detector. Similarly, the device may be configured to detect a measure of flow limitation, such as a fuzzy flow limitation measure as disclosed in PCT/AU008/000647, filed on May 9, 2008, (published as International Patent Application Publication No. (WO/2008/138040) and U.S. Provisional Patent Application No. 60/965,172 filed on Aug. 17, 2007, the disclosures of which are hereby incorporated herein by reference. In such embodiments, the determination of the reduction in ventilation (e.g., a classification associated with the sub-50 state) in conjunction with a detection of any one or more of a central apnea, patency of the airway, an absence of partial obstruction, an obstructive apnea or a low or insufficient measure of flow limitation, may be taken as a contra-indication of hypopnea condition. In such a case, the decrease in ventilation may be considered a result of apnea. For example, if a measure of partial obstruction or flow limitation indicates that there is insignificant or no obstruction during the sub-50 timing period, then rather than scoring a hypopnea, the detector may return to the start state (S0) or a further wait state (not shown) that provides a similar refractory timing period to wait for the ventilation measure to return above a threshold such as the 75% threshold discussed at 346. Similarly, by way of further example, if a measure of central apnea or airway patency indicates that there is a central apnea during the sub-50 timing period, then rather than scoring a hypopnea, the detector may return to the start state (S0) or the further wait state that provides a similar refractory timing period to wait for the ventilation measure to return above a threshold such as the 75% threshold discussed at 346. As a still further example, if a measure of obstructive apnea indicates that there is an obstructive apnea during the sub-50 timing period, then rather than scoring a hypopnea, the detector may return to the start state (S0) or the further wait state that provides a similar refractory timing period to wait for the ventilation measure to return above a threshold such as the 75% threshold discussed at 346.

Figure 4:
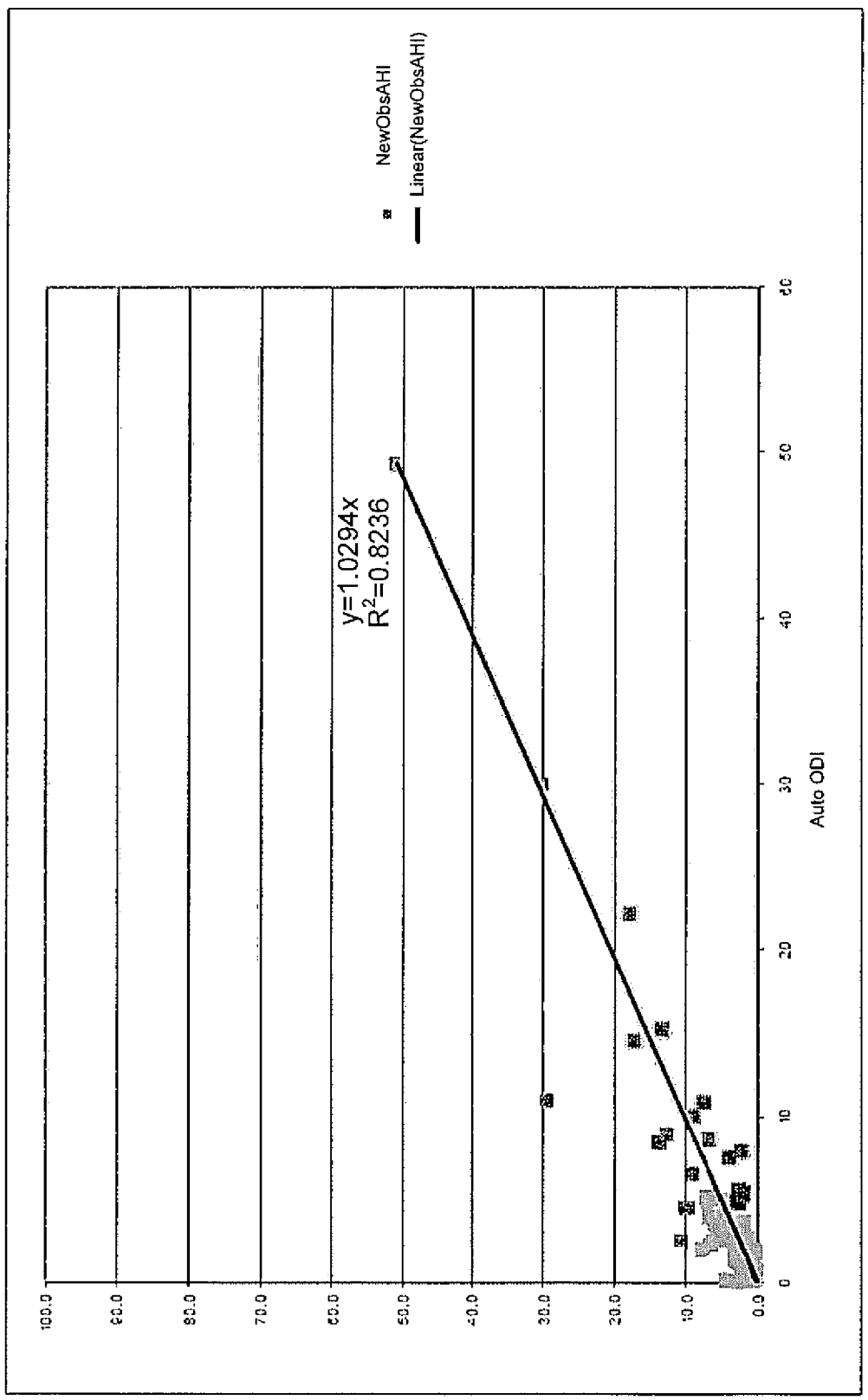
FIG. 4 is a graph illustrating a detection correlation of an example embodiment of the methodologies of the present technology.

An embodiment of the above detector based on the state diagram of FIG. 3 was tested on a library of data representing recorded patient respiratory flow signals. The flow data was pre-correlated with oxygen desaturation data. The hypopnea detector analyzed the flow data and hypopnea events were recorded. The hypopnea events detected were then correlated with the desaturation event data. A graph of the correlation is illustrated at FIG. 4. The graph shows that the hypopnea detection methodology correlates well with desaturation events (ODI) of at least a 4% desaturation.

In a further example of the scoring methodology illustrated in FIG. 3, the states of the state machine may be implemented to avoid scoring the hypopnea when apnea events (e.g., central apnea or obstructive apnea) are detected. For example, when the detector enters the scored state (S3), an hypopnea is merely "pre-logged" (such as by setting a "pre-logged" variable to true) so that it is not scored immediately. This may be considered the detection of a potential hypopnea by the detector. At this time, an apnea detector (such as an obstructive apnea and/or central apnea detector) may be polled (e.g., continuously during the state) to determine if the apnea detector has detected an apnea. If, in response to the polling, the detection of apnea has been confirmed, then the value of the "pre-logged" variable may be changed (e.g., set to false) and the state of the hypopnea detector is advanced to the super-75 state (S4) with the setting of the Super75 Timer at 348. In this way, the scoring of the hypopnea may be bypassed. Once the detector advances to the super-75 state (S4) then a potential hypopnea event will be logged or scored as an hypopnea event based on the pre-logged variable (e.g., if "pre-logged" variable is true, the event is logged as an hypopnea; but if the "pre-logged" variable is false, the event will not be logged or scored as a hypopnea.)

In this embodiment, the state machine of the detector advances out of the scored state (S3) by entering the super75 state (S4). Therefore, if at any time between entering the scored state and entering the super75 state (S4) an apnea is confirmed, then no hypopnea will be logged. Further, if at any time an apnea is confirmed before an hypopnea is scored, then the hypopnea detector is put into the refractory state and no score is possible until the refractory period is over. Thus, this embodiment can help to prevent false positive hypopnea scoring when a potential hypopnea event is an apnea event. While this embodiment implements a coordinated apnea and hypopnea detection by separate detectors (e.g., separate devices or separate software and/or hardware modules of a common apparatus) that communicate through polling as described above, in some embodiments, the states of the state machine above may be modified with additional thresholds intended for detecting apnea by known methods. In such a case, the output of a unified state machine of a common software and/or hardware module could be to detect either a hypopnea condition or an apnea condition depending on the results of the assessments of the various thresholds or conditions of the state machine.

(2) Additional Detection Features

Figure 5:
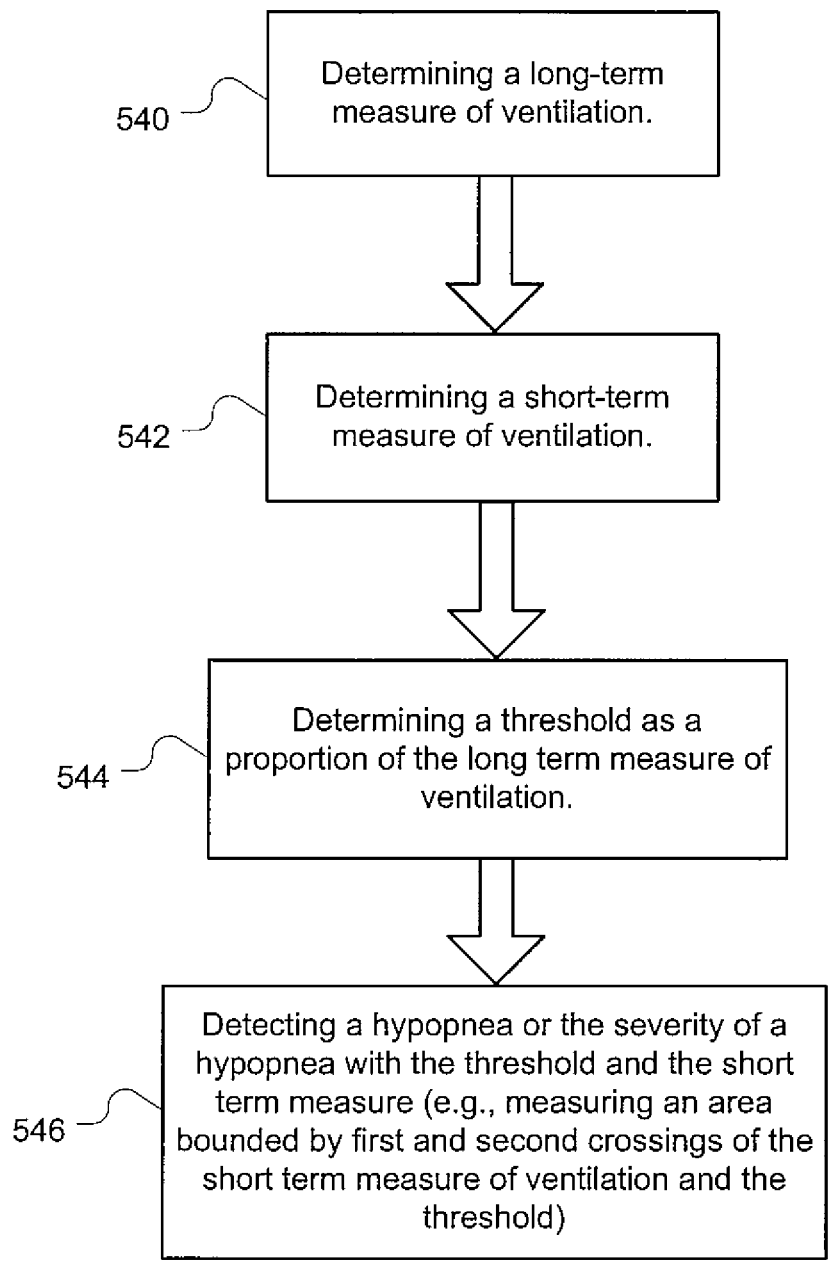
FIG. 5 is a further flow diagram of another example embodiment of a method of controlling an apparatus to detect a hypopnea and/or hypopnea severity.

In some embodiments, a scoring of a hypopnea may also include a determination of a measure of the severity of the scored hypopnea. An example of such a methodology is illustrated in FIG. 5. In the example, short-term and long-term measures of ventilation may be determined from a respiratory flow signal respectively at 540 and 542. For example, the measures may be an RMS ventilation or variance calculation as discussed in the prior embodiment determined over short and long time windows (e.g., about 12 and 60 seconds respectively). By way of further example, the ventilation measures may each be a low pass filtered average ventilation (e.g., half of the absolute value of data samples from a flow signal using short and long time constants). In still further embodiments, a long-term average tidal volume over multiple breaths and a recent tidal volume of one or an average of several breaths may be utilized as ventilation measures. At 544 a threshold as a function of the long-term measure is determined. For example, the threshold may be a portion or proportion of the measure (e.g., 50%, 75%, etc.). The threshold may be empirically determined based on hypopnea conditions in patients. Then at 546, the detection device detects a hypopnea or the severity of a hypopnea with the threshold and the short-term measure by, for example, measuring an area bounded by first and second crossings of the short-term measure of ventilation and the threshold.

Figure 6:
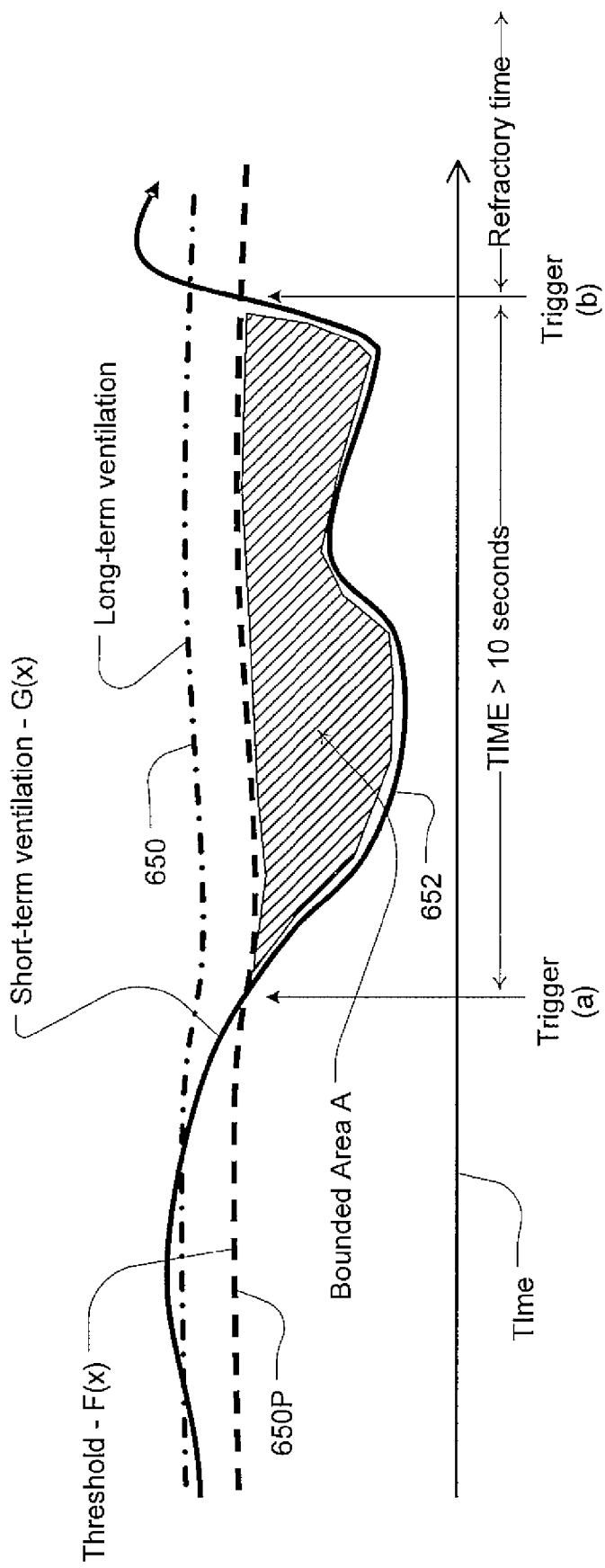
FIG. 6 is an illustration of a graph of a measure for detecting hypopnea and/or measuring an hypopnea severity.

An example of the technology may be considered in conjunction with the illustrated graph of FIG. 6. The graph plots a long-term ventilation measure 650 and a short-term ventilation measure 652, which may be determined from a measured respiratory flow signal. The graph also illustrates a threshold 650P determined as a function of the long-term ventilation measure. The extent of the bounded area A, which may provide a measure of severity of a hypopnea incident, may be determined by the detection device with the data from these measures. For example, this bounded area A may be determined by the following example formula:

$$A = \int_a^b f(x) - g(x) dx$$

Where:
f(x) is a proportion of a long-term measure of ventilation;
G(x) is the short-term measure of ventilation;
a and b are first and second crossings of f(x) and g(x), and may delimit a period of time at least ten seconds in length.

In an example embodiment, the integration of the ventilation measures may be implemented by sampling of these signals at a common time and by consecutively adding sample differences of the threshold and the short-term measure (i.e., f(x)−g(x), where x is a sample time) from time (a) to time (b). As shown in FIG. 6, the adding operation may be initiated (at "Trigger a") by comparing the threshold and the short-term measure to determine that the short-term measure is less than the threshold (e.g., G(x)<=F(x) at x=a). The adding operation may then stop (at "Trigger b") by again comparing the threshold and short-term ventilation (e.g., G(x)>=F(x) at x=b) to determine that the short-term measure has exceeded the threshold. The resulting sum may be taken as the severity measure. In some embodiments, if the time period over which samples were taken (e.g., a sample count) does not exceed a chosen time period indicative of hypopnea, such as about 10 seconds, the measure of severity may be disregarded (e.g., if (b−a)<10 seconds).

These area determination methods of FIG. 5 may optionally be implemented along with the scoring methodologies of FIGS. 2 and 3 to provide a severity measure for each scored event and/or to provide a joint hypoponea score based on both methodologies. For example, a hypopnea may be counted by a detector if either method or, alternatively, both methods detect the occurrence of a hypopnea. The severity measure may then be provided for the counted hypopnea. However, the area methods may also be implemented independent of the former methods as independent detectors.

Thus, the area measurement may be utilized to not only score a hypopnea but to provide a measure of its severity as well. For example, the severity measure may be compared to a threshold indicative of hypopnea. For example, a predetermined threshold may be empirically determined to be indicative of desaturation, such as about a 4% desaturation event. Thus, by comparing the severity measure to such a threshold, a hypopnea event may be scored. Optionally, its severity may be further analyzed or quantified by, for example, determining a value that it exceeds the threshold or as a ratio with the threshold. Still further, the value of the area itself may serve as the measure of severity.

In some embodiments, the length of the hypopnea, such as its time or duration, may also serve as a measure of severity. As with the area measure, it may be compared to one or more thresholds to assess the hypopnea event. In some embodiments, the area measure, the length or duration and the count, may be each analyzed to score a hypopnea and/or define its severity. For example, a hypopnea event scored by any of the described embodiments may be further characterized by its length and area to indicate severity.

In still further embodiments of the hypopnea detection technology, hypopnea events may be characterized or classified by type, such as by determining that an hypopnea event is an obstructive hypopnea or determining that the hypopnea event is a central hypopnea. In this way, the detector may distinguish between different types of hypopneas. For example, the common occurrence of (1) an hypopnea event detected by any of the methodologies herein, such as in the absence of a confirmation of a detected apnea, and (2) the detection of any one or more of (a) a measure of flow limitation (e.g., by analysis of a flow limitation index), (b) detecting a breath or breathing cycle during the hypopnea (e.g., confirming patient triggering of the transition from an expiration state to inspiration state based on triggering threshold) and/or (c) a measure of partial obstruction, may be collectively taken as a detection of an obstructive hypopnea for scoring rather than a central hypopnea. Similarly, the common occurrence of (1) a hypopnea event detected by any of the methodologies herein, such as in the absence of a confirmation of a detected apnea, and (2) the detection of any one or more of (a) a patency condition of the airway, (b) a failure to detect a breath or breathing cycle (e.g., an absence of patient triggering of the transition from an expiration state to inspiration state after a period of time based on triggering threshold) and/or (c) an absence of flow limitation or partial obstruction, may be collectively taken as a detection of an central hypopnea for scoring rather than an obstructive hypopnea. Thus, while a number of scored hypopnea events may be presented as a total of both obstructive hypopneas and central hypopneas, some embodiments of the present technology may also be implemented to score or report a break down of the number of obstructive hypopneas separately from the number of central hypopneas determined by the detector.

By way of further example, in one such embodiment of the detector, obstructive hypopnea events may be scored while hypopnea events that are attributable to central events are not scored. In the example, hypopnea events detected by any of the methods described herein that also coincide with a flow limitation index satisfying a desired threshold may be scored as a hypopnea or as an obstructive hypopnea. However, in the event that a detected hypopnea event coincides with the absence of a detection of a breath or breathing cycle, no hypopnea may be scored. In such a case the failure to detect a breath or breathing cycle (e.g., an absence of patient triggering of the transition from an expiration state to inspiration state after a period of time based on triggering threshold) may be considered an indicator of a central event (e.g., central apnea).

Example Architecture

Figure 7:
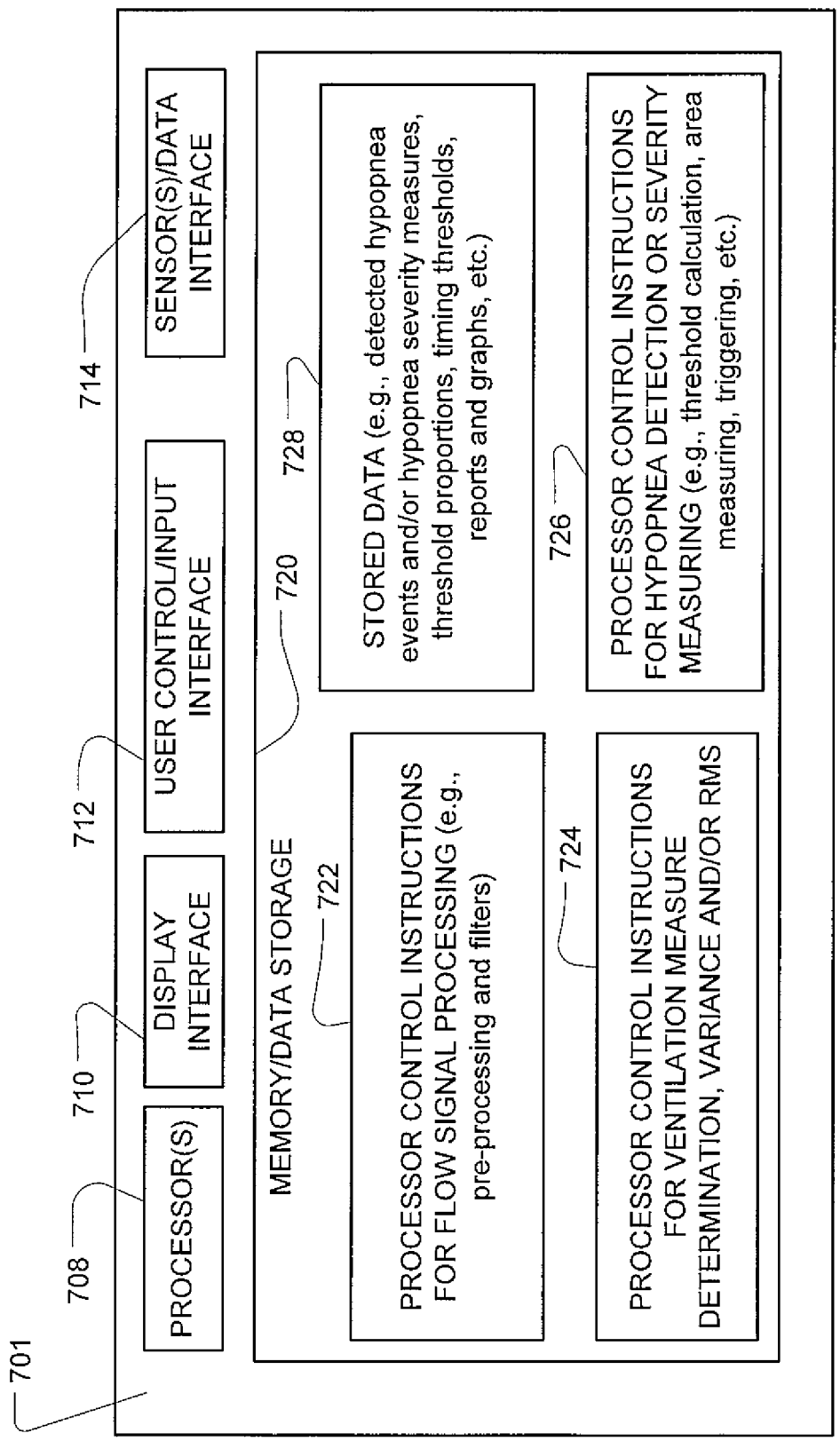
FIG. 7 is a block diagram of a controller in a hypopnea detection apparatus including example components thereof suitable for implementing the detection methodologies of the present technology.

An example system architecture of a controller is illustrated in the block diagram of FIG. 7. In the illustration, the hypopnea detection device 701 or general purpose computer may include one or more processors 708. The device may also include a display interface 710 to output hypopnea detection reports (e.g., hypopnea counts and/or severity measures), results or graphs (e.g., area curves as illustrated in FIG. 6) as described herein such as on a monitor or LCD panel. A user control/input interface 712, for example, for a keyboard, touch panel, control buttons, mouse etc. may also be provided to activate the methodologies described herein. The device may also include a sensor or data interface 714, such as a bus, for receiving/transmitting data such as programming instructions, oximetery data, flow data, hypopnea detection data etc. The device may also typically include a memory/data storage components containing control instructions of the aforementioned methodologies (e.g., FIGS. 2-6). These may include processor control instructions for flow or oximetery signal processing (e.g., pre-processing methods, filters) at 722 as discussed in more detail herein. They may also include processor control instructions for ventilation measure determination (e.g., variance, RMS calculations etc.) at 724. They may also include processor control instructions for Hypopnea detection or severity measurement (e.g., threshold determination, comparison, area measuring, triggering, timing methods, scoring etc.) at 726. Finally, they may also include stored data 728 for these methodologies such as detected hypopnea events and/or hypopnea severity measures, threshold proportions, timing thresholds, reports and graphs, etc.)

In some embodiments, the processor control instructions and data for controlling the above described methodologies may be contained in a computer readable recording medium as software for use by a general purpose computer so that the general purpose computer may serve as a specific purpose computer according to any of the methodologies discussed herein upon loading the software into the general purpose computer.

In the foregoing description and in the accompanying drawings, specific terminology, equations and drawing symbols are set forth to provide a thorough understanding of the present technology. In some instances, the terminology and symbols may imply specific details that are not required to practice the technology. For example, although the terms "first" and "second" have been used herein, unless otherwise specified, the language is not intended to provide any specified order but merely to assist in explaining distinct elements of the technology. Furthermore, although process steps in the detection methodologies have been illustrated in the figures in an order, such an ordering is not required. Those skilled in the art will recognize that such ordering may be modified and/or aspects thereof may be conducted in parallel.

Moreover, although the technology herein has been described with reference to particular embodiments, it is to be understood that these embodiments are merely illustrative of the principles and applications of the technology. It is therefore to be understood that numerous modifications may be made to the illustrative embodiments and that other arrangements may be devised without departing from the spirit and scope of the technology. For example, while the above scoring and severity measuring methodologies may be performed without measured blood oxygen data, in some embodiments, a detector may further include access to desaturation data from an oximetry sensor to classify hypopneas with actual $SpO_2$ data and ventilation or airflow data, such as by a method of the AASM guidelines. In such an embodiment, the detector may implement hypopnea detection with the $SpO_2$ data and without as described in prior embodiments (e.g., FIGS. 2, 3 and 5). Thus, the device may score a hypopnea by detection with either methodology or alternatively, with a detection by both methodologies. Such an embodiment may also be utilized to compare results from both methodologies to evaluate either methodology or to provide a treatment of the detected hypopneas if detected by either or both methodologies.

Additional example embodiments of the herein disclosed technology may also be understood upon consideration of the following descriptive paragraphs. To this end, the technology may also involve:

A method for controlling a processor to detect a hypopnea from a measured flow of breathable gas, the method of the processor comprising: determining a first measure from a short-term variance of data based on a measured flow of breathable gas; determining a second measure from a long-term variance of data based on a measured flow of breathable gas; comparing the first measure with first and second proportions of the second measure; and indicating a detection of the hypopnea based on the comparing if the first measure falls below the first proportion and does not subsequently exceed a range of the first and second proportions during a first time period.

The method of any of the proceeding paragraphs wherein the first proportion is less than the second proportion and further comprising indicating a detection of a hypopnea if the first measure does not exceed the first proportion during the first time period.

The method of any of the proceeding paragraphs wherein the first proportion is less than the second proportion and further comprising indicating a detection of a hypopnea if the first measure exceeds the first proportion but does not exceed the second proportion during the first time period.

The method of any of the proceeding paragraphs further comprising detecting a measure of flow limitation from a measured flow of breathable gas and wherein the indicating the detection of the hypopnea is further based on the measure of flow limitation being indicative of obstruction.

The method of any of the proceeding paragraphs wherein the comparing of the first measure and the first proportion represents a determination of whether an RMS value calculated from approximately ten to fifteen seconds of respiratory flow data falls below a threshold of approximately fifty percent of an RMS value calculated from approximately fifty to seventy seconds of respiratory flow data and wherein the first period of time is approximately three to eight seconds.

The method of any of the proceeding paragraphs wherein the comparing of the second measure and the second proportion represents a determination of whether an RMS value calculated from approximately ten to fifteen seconds of respiratory flow data is below a threshold of approximately seventy five percent of an RMS value calculated from approximately fifty to seventy seconds of respiratory flow data.

The method of any of the proceeding paragraphs wherein the comparing of the first measure and the first proportion represents a determination of whether an RMS value calculated from approximately ten to fifteen seconds of respiratory flow data falls below a threshold of approximately fifty percent of an RMS value calculated from approximately fifty to seventy seconds of respiratory flow data and wherein the first period of time is approximately three to eight seconds.

The method of any of the proceeding paragraphs further comprising impeding a further detection of a hypopnea until the first measure exceeds the second proportion during a second period of time.

The method of any of the proceeding paragraphs wherein the impeding of the further detection comprises comparing of the first measure and the second proportion, wherein this comparing represents a determination of whether an RMS value calculated from approximately ten to fifteen seconds of respiratory flow data exceeds a threshold of approximately seventy five percent of an RMS value calculated from approximately fifty to seventy seconds of respiratory flow data and wherein the second period of time is approximately ten to twenty seconds.

The method of any of the proceeding paragraphs further comprising measuring a flow of breathable gas with a flow sensor.

A hypopnea detection apparatus comprising: a controller having at least one processor to access data representing a measured flow of breathable gas, the controller being further configured to: determine a first measure from a short-term variance of the data; determine a second measure from a long-term variance of the data; compare the first measure with first and second proportions of the second measure; and indicate a detection of the hypopnea based on the comparing if the first measure falls below the first proportion and does not subsequently exceed a range of the first and second proportions during a first time period.

The apparatus of any of the proceeding paragraphs wherein the first proportion is less than the second proportion and wherein the controller is further configured to indicate a detection of a hypopnea if the first measure does not exceed the first proportion during the first time period.

The apparatus of any of the proceeding paragraphs wherein the first proportion is less than the second proportion and wherein the controller is further configured to indicate a detection of a hypopnea if the first measure exceeds the first proportion but does not exceed the second proportion during the first time period.

The apparatus of any of the proceeding paragraphs wherein the controller is further configured to detect a measure of flow limitation from the data and wherein the indicating the detection of the hypopnea is further based on the measure of flow limitation being indicative of obstruction.

The apparatus of any of the proceeding paragraphs wherein the comparing of the first measure and the first proportion represents a determination of whether an RMS value calculated from approximately ten to fifteen seconds of respiratory flow data falls below a threshold of approximately fifty percent of an RMS value calculated from approximately fifty to seventy seconds of respiratory flow data and wherein the first period of time is approximately three to eight seconds.

The apparatus of any of the proceeding paragraphs wherein the comparing of the second measure and the second proportion represents a determination of whether an RMS value calculated from approximately ten to fifteen seconds of respiratory flow data is below a threshold of approximately seventy five percent of an RMS value calculated from approximately fifty to seventy seconds of respiratory flow data.

The apparatus of any of the proceeding paragraphs wherein the comparing of the first measure and the first proportion represents a determination of whether an RMS value calculated from approximately ten to fifteen seconds of respiratory flow data falls below a threshold of approximately fifty percent of an RMS value calculated from approximately fifty to seventy seconds of respiratory flow data and wherein the first period of time is approximately three to eight seconds.

The apparatus of any of the proceeding paragraphs wherein the controller is further configured to impede a further detection of a hypopnea until the first measure exceeds the second proportion during a second period of time.

The apparatus of any of the proceeding paragraphs wherein the impeding of the further detection comprises comparing of the first measure and the second proportion, wherein this comparing represents a determination of whether an RMS value calculated from approximately ten to fifteen seconds of respiratory flow data exceeds a threshold of approximately seventy five percent of an RMS value calculated from approximately fifty to seventy seconds of respiratory flow data and wherein the second period of time is approximately ten to twenty seconds.

The apparatus of any of the proceeding paragraphs further comprising a flow sensor and wherein the controller is further configured to determine the measured flow of breathable gas with the flow sensor.

The apparatus of any of the proceeding paragraphs further comprising: a flow generator configured to produce a breathable gas for a patient at a pressure above atmospheric pressure; wherein the controller is further configured to control the flow generator to produce the breathable gas according to a pressure therapy regime based on the detected hypopnea.

A method for controlling a processor to detect a hypopnea from a measured flow of breathable gas, the method of the processor comprising: determining a long-term measure of ventilation; determining a short-term measure of ventilation; determining a threshold as a proportion of the long-term measure of ventilation; measuring an area bounded by first and second crossings of the short-term measure of ventilation and the threshold; and detecting the hypopnea with the measured area.

The method of any of the preceding paragraphs wherein the measuring comprises integrating a difference between the threshold and the short-term measure of ventilation during a time period from when the short-term measure falls below the threshold to when the short-term measure exceeds the threshold.

The method of any of the preceding paragraphs wherein the measuring comprises adding a plurality of sample differences during a time period from when the short-term measure falls below the threshold to when the short-term measure exceeds the threshold, wherein each sample difference is a difference between a sample of the threshold and a sample of the short-term measure of ventilation.

The method of any of the preceding paragraphs further comprising impeding a further detection of a hypopnea during a refractory period initiated at the second crossing.

The method of any of the preceding paragraphs further comprising triggering the measuring of the area upon detecting the first crossing by comparing the short-term measure of ventilation and the threshold for inequality.

The method of any of the preceding paragraphs wherein the detecting of the hypopnea is contingent upon a time from the first crossing to the second crossing exceeding about ten seconds.

The method of any of the preceding paragraphs wherein the short-term measure of ventilation comprises an output of low pass filtering half of an absolute value of a measure of flow of breathable gas with a first time constant.

The method of any of the preceding paragraphs wherein the long-term measure of ventilation comprises an output of low pass filtering half of an absolute value of a measure of flow of breathable gas with a second time constant, the second time constant being larger than the first time constant.

The method of any of the preceding paragraphs wherein the proportion comprises approximately seventy percent.

The method of any of the preceding paragraphs further comprising indicating a severity of the hypopnea with the measure of area.

The method of any of the preceding paragraphs wherein the detecting comprises comparing the measured area with a threshold chosen to be approximately indicative of a desaturation of blood oxygen of at least four percent.

The method of any of the preceding paragraphs further comprising measuring a flow of breathable gas with a flow sensor.

The method of any of the preceding paragraphs further comprising detecting a measure of flow limitation from the measured flow signal and wherein the detection of the hypopnea is further based on the measure of flow limitation being indicative of obstruction.

An apparatus to detect a hypopnea from a measured flow of breathable gas, the apparatus comprising: a controller having at least one processor to access data representing a measured flow of breathable gas, the controller being further configured to: determine a long-term measure of ventilation from the measured flow; determine a short-term measure of ventilation from the measured flow; determine a threshold as a proportion of the long-term measure of ventilation; measure an area bounded by first and second crossings of the short-term measure of ventilation and the threshold; and detect the hypopnea with the measured area.

The apparatus of any of the preceding paragraphs wherein the controller is configured to measure the area by integrating a difference between the threshold and the short-term measure of ventilation during a time period from when the short-term measure falls below the threshold to when the short-term measure exceeds the threshold.

The apparatus of any of the preceding paragraphs wherein the controller is configured to measure the area by adding a plurality of sample differences during a time period from when the short-term measure falls below the threshold to when the short-term measure exceeds the threshold, wherein each sample difference is a difference between a sample of the threshold and a sample of the short-term measure of ventilation.

The apparatus of any of the preceding paragraphs wherein the controller is further configured to impede a further detection of a hypopnea during a refractory period initiated by detection of the second crossing.

The apparatus of any of the preceding paragraphs wherein the controller is further configured to trigger the measuring of the area upon detecting the first crossing by comparing the short-term measure of ventilation and the threshold for inequality.

The apparatus of any of the preceding paragraphs wherein the detection of the hypopnea is contingent upon a time from the first crossing to the second crossing exceeding about ten seconds.

The apparatus of any of the preceding paragraphs wherein the short-term measure of ventilation comprises an output of low pass filtering half of an absolute value of a measure of flow of breathable gas with a first time constant.

The apparatus of any of the preceding paragraphs wherein the long-term measure of ventilation comprises an output of low pass filtering half of an absolute value of a measure of flow of breathable gas with a second time constant, the second time constant being larger than the first time constant.

The apparatus of any of the preceding paragraphs wherein the proportion comprises approximately seventy percent.

The apparatus of any of the preceding paragraphs wherein the controller is further configured to indicate a severity of the hypopnea with the measure of area.

The apparatus of any of the preceding paragraphs wherein the detecting comprises comparing the measured area with a threshold chosen to be approximately indicative of a desaturation of blood oxygen of at least four percent.

The apparatus of any of the preceding paragraphs wherein the controller is further configured to detect a measure of flow limitation from the data and wherein the detection of the hypopnea is further based on the measure of flow limitation being indicative of obstruction.

The apparatus of any of the preceding paragraphs further comprising a flow sensor and wherein the controller is further configured to determine the measured flow of breathable gas with the flow sensor.

The apparatus of any of the preceding paragraphs further comprising: a flow generator configured to produce a breathable gas for a patient at a pressure above atmospheric pressure; wherein the controller is further configured to control the flow generator to produce the breathable gas according to a pressure therapy regime based on the detected hypopnea.

A method for controlling a processor to detect a hypopnea from a measured flow of breathable gas, the method of the processor comprising: determining a long-term measure of ventilation; determining a short-term measure of ventilation; determining a threshold as a proportion of the long-term measure of ventilation; calculating an extent of a hypopnea as a function of the short-term measure of ventilation and the threshold; and indicating a severity of the hypopnea with the measured extent.

The method of any of the preceding paragraphs wherein the indicating comprises outputting a value of the measured extent.

The method of any of the preceding paragraphs wherein the calculated extent is a calculated area bounded by first and second crossings of the short-term measure of ventilation and the threshold.

The method of any of the preceding paragraphs further comprising comparing the calculated area with a threshold chosen to be approximately indicative of a desaturation of blood oxygen of at least four percent.

The method of any of the preceding paragraphs further comprising measuring a flow of breathable gas with a flow sensor.

The method of any of the preceding paragraphs further comprising detecting a measure of flow limitation from the measure flow and wherein the indicating the detection of the hypopnea is further based on the measure of flow limitation being indicative of obstruction.

An apparatus to detect a hypopnea from a measured flow of breathable gas, the apparatus comprising: a controller having at least one processor to access data representing a measured flow of breathable gas, the controller being further configured to: determine a long-term measure of ventilation from the data; determine a short-term measure of ventilation from the data; determine a threshold as a proportion of the long-term measure of ventilation; calculate an extent of a hypopnea as a function of the short-term measure of ventilation and the threshold; and indicate a severity of the hypopnea with the calculated extent.

The apparatus of any of the preceding paragraphs wherein the controller is configured to indicate the severity by outputting a value of the calculated extent to an output device.

The apparatus of any of the preceding paragraphs wherein the controller calculates the extent by calculating an area bounded by first and second crossings of the short-term measure of ventilation and the threshold.

The apparatus of any of the preceding paragraphs wherein the controller is further configured to compare the calculated area with a threshold chosen to be approximately indicative of a desaturation of blood oxygen of at least four percent.

The apparatus of any of the preceding paragraphs further comprising a flow sensor and wherein the controller is further configured to determine the measured flow of breathable gas with the flow sensor.

The apparatus of any of the preceding paragraphs further comprising: a flow generator configured to produce a breathable gas for a patient at a pressure above atmospheric pressure; wherein the controller is further configured to control the flow generator to produce the breathable gas according to a pressure therapy regime based on the detected hypopnea.

The apparatus of any of the preceding paragraphs wherein the controller is further configured to detect a measure of flow limitation from the data and wherein the indicating the detection of the hypopnea is further based on the measure of flow limitation being indicative of obstruction.

A method for controlling a processor to classify a hypopnea from a measured flow of breathable gas, the method of the processor comprising: detecting an hypopnea event from a measured flow of breathable gas; determining a measure indicative of obstruction in the measured flow coincident with the hypopnea event; and classifying the detected hypopnea event as obstructive or central based on the determining of the measure indicative of obstruction.

The method of any of the preceding paragraphs wherein the determining comprises detecting partial obstruction and the classifying comprises scoring an obstructive hypopnea event.

The method of any of the preceding paragraphs further comprising detecting an absence of a breath and the classifying comprises scoring a central hypopnea event.

The method of any of the preceding paragraphs further comprising detecting an absence of a breath coincident with a further detected hypopnea event and refraining from scoring the further detected hypopnea event based on the detected absence of a breath.

A hypopnea detection apparatus comprising: a controller having at least one processor to access data representing a measured flow of breathable gas, the controller being further configured to control: a detection of an hypopnea event from the data representing the measured flow of breathable gas; a determination of a measure indicative of obstruction coincident with the hypopnea event in the data representing the measured flow; and a classification the detected hypopnea event as obstructive or central based on the determining of the measure indicative of obstruction.

The apparatus of any of the preceding paragraphs wherein the determination detects partial obstruction and the classification comprises scoring an obstructive hypopnea event.

The apparatus of any of the preceding paragraphs wherein the controller is further configured to control a detection of an absence of a breath and the classification comprises scoring a central hypopnea event.

The apparatus of any of the preceding paragraphs wherein the controller is further configured to detect an absence of a breath coincident with a further detected hypopnea event and to refrain from scoring the further detected hypopnea event based on the detected absence of a breath.

The apparatus of any of the preceding paragraphs further comprising: a flow generator configured to produce a breathable gas for a patient at a pressure above atmospheric pressure; and a flow sensor, wherein the controller is further configured to measure the flow of breathable gas with the flow sensor and to control the flow generator to produce the breathable gas according to a pressure therapy regime based on the detected hypopnea.

The invention claimed is:

1. A hypopnea detection apparatus comprising:
  a controller having at least one processor to access data representing a measured flow of breathable gas, the controller being further configured to:
    determine a first measure from the flow data, the measure representing a short-term ventilation;
    determine a second measure from the flow data, the measure representing a long-term ventilation;
    compare the first measure with first and second proportions of the second measure; and
    indicate a detection of the hypopnea based on the comparing if the first measure is below the first proportion at a start and an end of a first time period, while remaining below the second proportion throughout the first time period.

2. The apparatus of claim 1 wherein the first proportion is less than the second proportion and wherein the controller is further configured to indicate a detection of a hypopnea if the first measure does not exceed the first proportion during the first time period.

3. The apparatus of claim 1 wherein the first proportion is less than the second proportion and wherein the controller is further configured to indicate a detection of a hypopnea if the first measure exceeds the first proportion but does not exceed the second proportion during the first time period.

4. The apparatus of claim 1 wherein the controller is further configured to detect a measure of flow limitation from the data and wherein the indicating the detection of the hypopnea is further based on the measure of flow limitation being indicative of obstruction.

5. The apparatus of claim 1 wherein the comparing of the first measure and the first proportion represents a determination of whether an RMS value calculated from approximately ten to fifteen seconds of respiratory flow data falls below a threshold of approximately fifty percent of an RMS value calculated from approximately fifty to seventy seconds of respiratory flow data and wherein the first period of time is approximately three to eight seconds.

6. The apparatus of claim 1 wherein the comparing of the first measure and the second proportion represents a determination of whether an RMS value calculated from approximately ten to fifteen seconds of respiratory flow data is below a threshold of approximately seventy five percent of an RMS value calculated from approximately fifty to seventy seconds of respiratory flow data.

7. The apparatus of claim 6 wherein the comparing of the first measure and the first proportion represents a determination of whether an RMS value calculated from approximately ten to fifteen seconds of respiratory flow data falls below a threshold of approximately fifty percent of an RMS value calculated from approximately fifty to seventy seconds of respiratory flow data and wherein the first period of time is approximately three to eight seconds.

8. The apparatus of claim 1 wherein the controller is further configured to impede a further detection of a hypopnea until the first measure exceeds the second proportion during a second period of time.

9. The apparatus of claim 8 wherein the impeding of the further detection comprises comparing of the first measure and the second proportion, wherein this comparing represents a determination of whether an RMS value calculated from approximately ten to fifteen seconds of respiratory flow data exceeds a threshold of approximately seventy five percent of an RMS value calculated from approximately fifty to seventy seconds of respiratory flow data and wherein the second period of time is approximately ten to twenty seconds.

10. The apparatus of claim 1 further comprising a flow sensor and wherein the controller is further configured to determine the measured flow of breathable gas with the flow sensor.

11. The apparatus of claim 10 further comprising:
  a flow generator configured to produce a breathable gas for a patient at a pressure above atmospheric pressure; wherein the controller is further configured to control the flow generator to produce the breathable gas according to a pressure therapy regime based on the detected hypopnea.

12. The apparatus of claim 1 wherein the first measure is a short-term variance and the second measure is a long-term variance.

13. The hypopnea detection apparatus of claim 1 wherein the controller is further configured to indicate a detection of the hypopnea based on the comparing if the first measure falls below the first proportion and enters but does not subsequently exceed a range of the first and second proportions, the indication being during the first time period when the first measure subsequently falls below the first and second proportions.

14. A hypopnea detection method comprising:
  with a processor to access data representing a measured flow of breathable gas:
    determining a first measure from the flow data, the measure representing a short-term ventilation;
    determining a second measure from the flow data, the measure representing a long-term ventilation;
    comparing the first measure with first and second proportions of the second measure; and
    indicating a detection of the hypopnea based on the comparing if the first measure is below the first proportion at a start and an end of a first time period, while remaining below the second proportion throughout the first time period.

15. The method of claim 14 wherein the first proportion is less than the second proportion and wherein the processor indicates a detection of a hypopnea if the first measure does not exceed the first proportion during the first time period.

16. The method of claim 14 wherein the first proportion is less than the second proportion and wherein the processor indicates a detection of a hypopnea if the first measure exceeds the first proportion but does not exceed the second proportion during the first time period.

17. The method of claim 14 wherein the processor detects a measure of flow limitation from the data and wherein the indicating the detection of the hypopnea is further based on the measure of flow limitation being indicative of obstruction.

18. The method of claim 14 wherein the comparing of the first measure and the first proportion represents a determination of whether an RMS value calculated from approximately ten to fifteen seconds of respiratory flow data falls below a threshold of approximately fifty percent of an RMS value calculated from approximately fifty to seventy seconds of respiratory flow data and wherein the first period of time is approximately three to eight seconds.

19. The method of claim 14 wherein the comparing of the first measure and the second proportion represents a determination of whether an RMS value calculated from approximately ten to fifteen seconds of respiratory flow data is below a threshold of approximately seventy five percent of an RMS value calculated from approximately fifty to seventy seconds of respiratory flow data.

20. The method of claim 19 wherein the comparing of the first measure and the first proportion represents a determination of whether an RMS value calculated from approximately ten to fifteen seconds of respiratory flow data falls below a threshold of approximately fifty percent of an RMS value calculated from approximately fifty to seventy seconds of respiratory flow data and wherein the first period of time is approximately three to eight seconds.

21. The method of claim 14 further comprising with the processor impeding a further detection of a hypopnea until the first measure exceeds the second proportion during a second period of time.

22. The method of claim 21 wherein the impeding of the further detection comprises comparing of the first measure and the second proportion, wherein this comparing represents a determination of whether an RMS value calculated from approximately ten to fifteen seconds of respiratory flow data exceeds a threshold of approximately seventy five percent of an RMS value calculated from approximately fifty to seventy seconds of respiratory flow data and wherein the second period of time is approximately ten to twenty seconds.

23. The method of claim 14 further comprising measuring with a sensor a breathable gas to determine the measured flow.

24. The method of claim 23 further comprising controlling with the processor a flow generator configured to produce a breathable gas for a patient at a pressure above atmospheric pressure, the controlling comprising setting the flow generator to produce the breathable gas according to a pressure therapy regime based on the detected hypopnea.

25. The method of claim 14 wherein the first measure is a short-term variance and the second measure is a long-term variance.

26. The hypopnea detection method of claim 14 further comprising with the processor indicating a detection of the hypopnea based on the comparing if the first measure falls below the first proportion and enters but does not subsequently exceed a range of the first and second proportions, the indication being during the first time period when the first measure subsequently falls below the first and second proportions.

* * * * *